United States Patent [19]

Gerber

[11] Patent Number: 5,003,500

[45] Date of Patent: Mar. 26, 1991

[54] PROCESS AND APPARATUS FOR THE PREPARATION OF COLOR FORMULATIONS UTILIZING POLARIZED LIGHT IN SPECTROPHOTOMETRY

[75] Inventor: Werner H. Gerber, Riehen, Switzerland

[73] Assignee: Ciba-Geigy Corporation, Ardsley, N.Y.

[21] Appl. No.: 398,278

[22] Filed: Aug. 24, 1989

[30] Foreign Application Priority Data

Sep. 5, 1988 [CH] Switzerland ............... 3309/88

[51] Int. Cl.$^5$ ............ G01J 3/46; G01J 3/02; G01N 21/25
[52] U.S. Cl. ................. 364/526; 356/402; 356/446
[58] Field of Search ........... 364/526, 556; 356/369, 356/364, 402, 446

[56] References Cited

U.S. PATENT DOCUMENTS 3,601,589  8/1971  McCarty ................. 364/526 X
4,866,264  9/1989  Biricik et al. ........... 356/369 X
4,890,926  1/1990  Dosmann et al. .......... 356/369

OTHER PUBLICATIONS

"The Effect of Measuring Geometry on Computer Color Matching", by Danny C. Rich, Color Research and Application, vol. 13, No. 2, pp. 113–118, Apr. 1988.
"Comparison of Different Theoretical Models of Multiple Scattering for Pigmented Media", by Pauli and Eitle, from Colour, 73 Adam Hilger, London 1973.
"High Precision Scanning Ellipsometer", by Aspnes and Studna, Applied Optics/vol. 14, No. 1/220–228/-Jan. 1975.
IBM Technical Disclosure Bulletin, (Jaerisch et al), vol. 27, No. 9, 5472–5473, Feb., 1985.

Primary Examiner—Parshotam & Lall
Assistant Examiner—S. A. Melnick
Attorney, Agent, or Firm—Burns, Doane, Swecker & Mathis

[57] ABSTRACT

A process and an apparatus for the preparation of color formula for the reproduction of the color of a master are described. In the process, during a measurement, the gloss component of the reflected light is already suppressed with polarizing filters, so that the calculation of the colorant concentrations may be carried out independently of the surface conditions of the master to be reproduced (glossy, semigloss, matte) with a set of optical data of the colorants that are independent of surface conditions.

10 Claims, 3 Drawing Sheets

PROCESS AND APPARATUS FOR THE PREPARATION OF COLOR FORMULATIONS UTILIZING POLARIZED LIGHT IN SPECTROPHOTOMETRY

BACKGROUND OF THE INVENTION

The invention concerns a process and apparatus for the preparation of color recipes. More specifically, the present invention relates to a process and apparatus for preparing a color formula for the reproduction of the color of a master by mixing suitable concentrations of colorants, in particular colorings and pigments, wherein the master is exposed by a source of directional measuring light, and the light directionally reflected by the master is passed after spectral decomposition to a detector which produces spectral measuring data from the reflected light. The measured data are converted by a computer unit into concentrations of colorants having known optical data previously determined by spectrophotometric analysis via calibrated colorations using known standard colorant concentrations. A sample, adjusted in accordance with the colorant concentrations calculated spectrophotometrically, is compared with the master, and the colorant concentrations corrected in keeping with the differences measured, this correction process being repeated until the difference measured is less than a predetermined minimum color deviation.

The preparation of color recipes, i.e. the calculation of the appropriate concentrations of colorants or pigments, to reproduce the color of a master, is one of the most important tasks in the industrial processing of colorants. In particular in the textile, printing, automotive and plastic industries, requirements relative to the accuracy and reproducibility of colors are high. For this reason colorimetric measurements represent an exceedingly useful and indispensable instrument in the quality control of colored products and the colorants required (colors, pigments) and the preparation of color recipes.

In an article by Dr. Ludwig Gall in "Farbe und Lack", Vol. 80, No. 4, 1974, pages 297–306, the principal process for the preparation of color recipes is described. The master to be reproduced relative to color is spectrophotometrically analyzed and the measured data determined converted in a computer unit into concentration proportions of colorants (colors, pigments) of known optical data, such as for example absorption and scatter coefficients. The quality and accuracy of the colorant concentrations determined depends on the accuracy of the knowledge of the optical data of the colorants available. For this purpose, standard colorings are prepared for each colorant with different, accurately known colorant concentrations and analyzed by spectrophotometry. The wavelength dependent optical data (absorption and scatter coefficient) of each colorant as a function of the colorant concentration are stored in a memory unit for use in the calculation of colorant concentration for the master to be reproduced in color.

The surface state of the sample (this could be a calibration coloring, a master or a reproduction) significantly affects the measured results and thus the optical data and the colorant concentrations determined. These boundary surface effects of the boundary layer between surrounding media and the sample surface are known generally as gloss effects and become apparent as a more or less glossy or matte surface of the sample. In the integrating-sphere measuring geometries usually employed (for example d/8, 8/d, ... ; the number or symbol preceding the slash refers to the angle enclosed between the incident light and a normal onto the sample surface, while the number or symbol following it designates the angle between the reflected light and the normal; d signifies diffuse), the entire gloss component of the reflected light is included. This gloss component in the heretofore most frequently used color formulation method according to the Kubelka-Munk two-constant theory with the inclusion of the Saunderson approximation (article by Dr. Ludwig Gall in "Farbe und Lack", Vol. 80, No. 4, 1974, pages 297–306 and "Practical Color Measuring Course", Bundesanstalt für Materialprü fung [Federal Material Testing Institute], DK 535.64/.65, 1982 Edition, pages 53–57) is taken into account in that depending on the surface characteristics (a distinction may be made for example between glossy, semigloss or matte surface classes) of the master to be matched, color formulation is carried out with reference to an appropriate set of optical data, from glossy, semigloss or matte calibrating colorations. It is also necessary to determine a separate wavelength dependent optical data set for each type of surface characteristic. This requirement results in an enormous preparatory analysis effort for all available colorants, as in addition, every calibrating and measuring process is repeated up to five times or more for every surface class of the calibrating colorations, in order to obtain adequate statistical certainty. Processes based essentially on the approximations of Kubelka-Munk and Saunderson are described for example in U.S. Pat. No. 3,601,589 and in JP-A-62-90518. In EP-A-065,484 and DE-A-1,547,467, respectively, a reflectance color measuring instrument and a photoelectric color brightness comparison instrument are described, in which direct surface reflections are blocked out by crossed polarizers.

In the known measuring devices highly different measuring geometries are employed. In a publication in "Color research and application", Vol. 13, No. 2, Apr. 1988, pages 113–118, Danny C. Rich describes the effect of the measuring geometry on color matching. As the result of a comparative experiment between integrating-sphere geometries and bidirectional geometries, in particular 0/45 geometries, such as those described for example in the German standard DIN 5033, Part 7, Jul. 1983, he came to the conclusion that the 0/45 geometry (and thus the equivalent 45/0 geometry) is superior to the integrating-sphere geometry (d/8). As shown by these comparative experiments by Rich, the different sample surface characteristics may be taken into account by means of separate surface dependent optical data sets of colorants, in bidirectional measuring processes also.

A first attempt to move away from this enormous preparatory analytical effort, is represented by a calculation method based on the three-beam theory of Dr. H. Pauli and Dr. D. Eitle (Colour 73, Adam Hilger, London 1973, pages 423 to 426 and a preprint of a pertinent paper presented at the FATIPEC XIV Congress, Budapest 1978, pages 209–213), in which the gloss component is taken into account empirically in the calculation of the colorant concentration, and therefore is able to work with a single surface state dependent set of optical data (wavelength dependent), independently of the surface characteristics of the colored master to be matched. However, it has been necessary heretofore in this process also to determine the entire gloss component, both in the analysis of the colored master and in the determination of the optical data of the colorants, by means of an involved integrating-sphere measuring geometry.

The above described processes for the preparation of color formulations on the one hand have the disadvantage of a high preparatory analytical effort of the colorants, with wavelength dependent optical data sets of the colorants differing as a function of surface characteristics and of different measuring layouts and depending on the type of measuring geometry. On the other hand, integrating spheres with the usual diameters of up to about 20 cm and more, together with the associated peripherals (computer unit, etc.) are very cumbersome and heavy and may be located stationarily in a central laboratory only. There is, however, a need to have available a mobile measuring apparatus and process for "on site" measurements and color formulations.

SUMMARY OF THE INVENTION

Accordingly, an object of the present invention is the provision of a process for the preparation of color formulations, whereby independently of the state of the master surface and the type of the calculation method used, it is possible to work with a single set of optical data (wavelength dependent) independently of surface conditions. In addition to this universal applicability of the process, it should also be possible to apply the process in a mobile manner and "on site". The measuring layout should therefore be readily handled and transportable.

This object is attained by a process and apparatus for the preparation of color formulations for the reproduction of the color of a master by the mixing of suitable concentrations of colorants, in particular colorings and pigments, wherein a measuring light is polarized in a first polarizer prior to impacting a sample, the reflected light being passed by a wavelength dispersing element through a second polarizer serving as an analyzer prior to its spectral decomposition, and wherein optical data of the colorants used for the determination of the colorant concentrations desired is independent of surface conditions. Preferred variants of the process and apparatus are also set forth below.

BRIEF DESCRIPTION OF THE DRAWINGS

A better understanding of the process according to the present invention and the corresponding apparatus for the spectrophotometric analysis of colored samples and the preparation of color formulations will become more apparent from the following Detailed Description of the Preferred Embodiments when read in conjunction with reference to the drawings wherein.

DETAILED DESCRIPTION OF PREFERRED EMBODIMENTS

Figure 1:
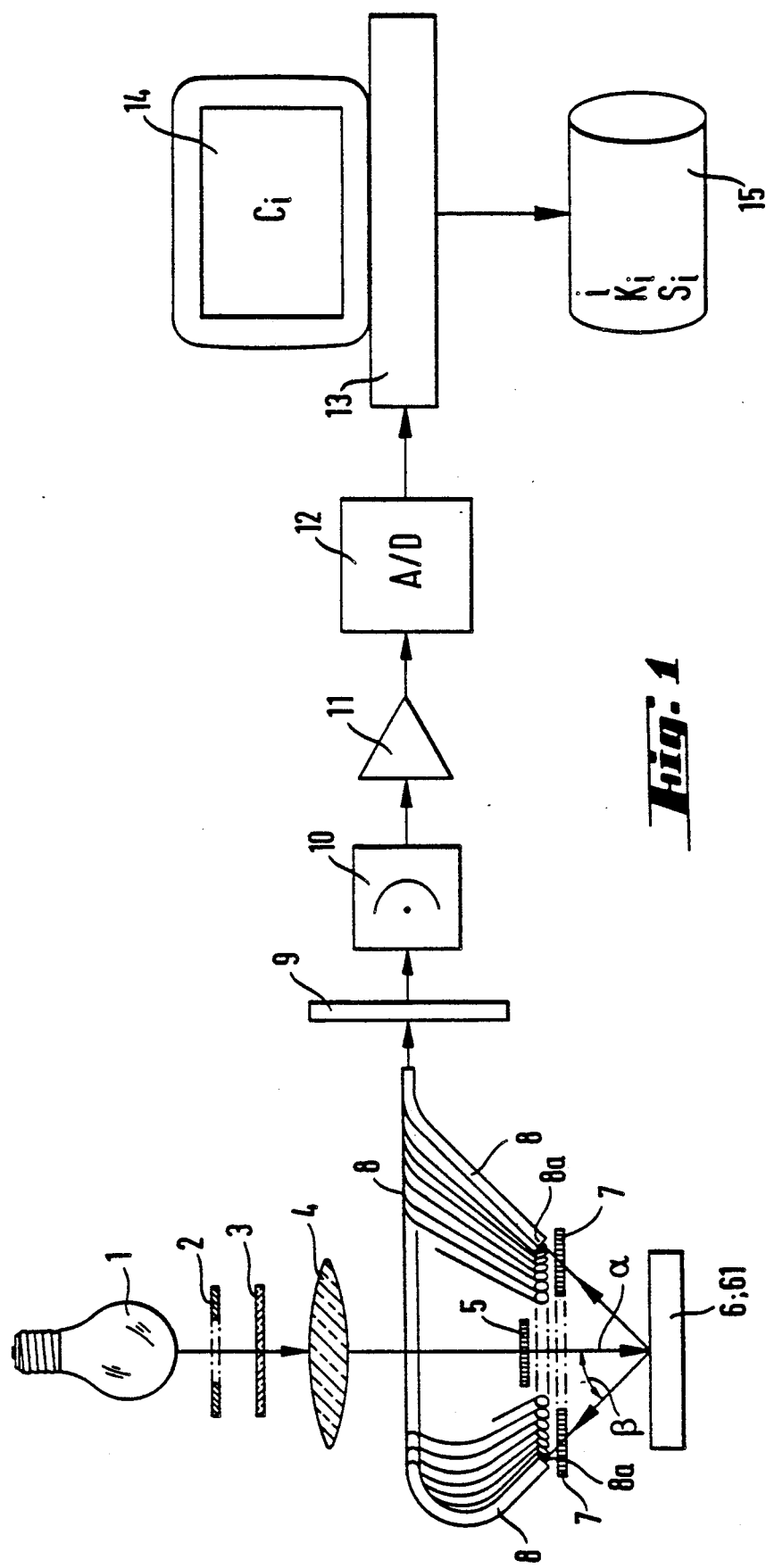
FIG. 1 shows the fundamental layout of an exemplary embodiment of the apparatus according to the present invention.

FIG. 1 shows the fundamental measuring and analysis layout for the preparation of color formulations. It consists of a so-called bidirectionally oriented measuring layout and in particular a 0°/45° measuring geometry is represented. This signifies that the measuring light is beamed at an angle $\alpha$ of about $0°\pm10°$ to the normal onto a sample (master 6 or reset 61) and the component reflected all around at an angle $\beta$ of about $45°\pm5°$ is detected and passed to a detector 10.

The beam of light emitted by a polychromatic source of light 1 is limited in its width by a diaphragm 2. In order to compensate possible fluctuations of the spectral emission of the light source 1, the light is passed through a standard filter 3, so that the spectrum of the measuring light radiated onto the sample (master 6 or set 61) has a defined composition. By means of an imaging optical device 4 the light source 1 is reproduced on the sample 6, 61. Immediately preceding the sample 6, 61 a first polarizer 5 is located, through which the measuring light must pass, so that only polarized measuring light is incident at an angle $\alpha$ of $0°\pm10°$ to the normal onto the sample 6, 61. Of the light reflected all around, according to the exemplary embodiment, only the component reflected at an angle $\beta$ of $45°\pm5°$ is detected. This is effected, for example, by means of a suitable annular layout of an optical fiber bundle 8. Immediately prior to the inlet 8a into the individual fibers of the optical fiber bundle 8, a preferably annular second polarizer 7 is located, serving as the analyzer for the reflected light. By means of this second polarizer 7, the gloss component depending on the surface condition of the sample 6, 61 of the reflected light may be suppressed. By the optical fiber bundle 8, the reflected light is passed to a wavelength dispersing element 9. This wavelength dispersing element may be a grating, a filter or a prism. Upon its passage through said wavelength dispersing element 9, the reflected light is spectrally decomposed and immediately after acquired by a detector 10. This detector may consist of a single photosensitive diode which is scanned for the detection of the spectral component of the reflected light, but it may also consist of a linear array of several photodiodes. The light wave dependent electric signals ($R(\lambda)$) supplied by the detector 10 are amplified in an amplifier 11 and passed to an analog/digital converter 12.

All of the above described components of the measuring layout are preferably combined in a single measuring apparatus, preferably with serial interfaces. The measuring geometry is not restricted to the 0°/45° geometry shown as an example in FIG. 1, but may also be a 45°/0° geometry, which is closest to visual viewing. A highly compact spectrophotometer of this type, SPM 100, is described in a prospectus of Gretag AG, Regensdorf/Zürich, Gretag 98.20.58 SP 8806.

The digitalized measured results $R(\lambda)$ are fed into a computer unit 13 and therein converted together with the optical data which were determined from the spectrophotometric analysis of calibrated colorations (absorption coefficient $K_i$ and scatter coefficient $S_i$) of the available colorants i and stored in a memory unit 15, into colorant combinations $C_i$. The colorant concentration $C_i$, as the end result of calculating processes to be described hereafter, are listed in and output via unit 14 (screen, printer), and represent the color formulation for the colored master 6 to be reproduced.

Figure 2:
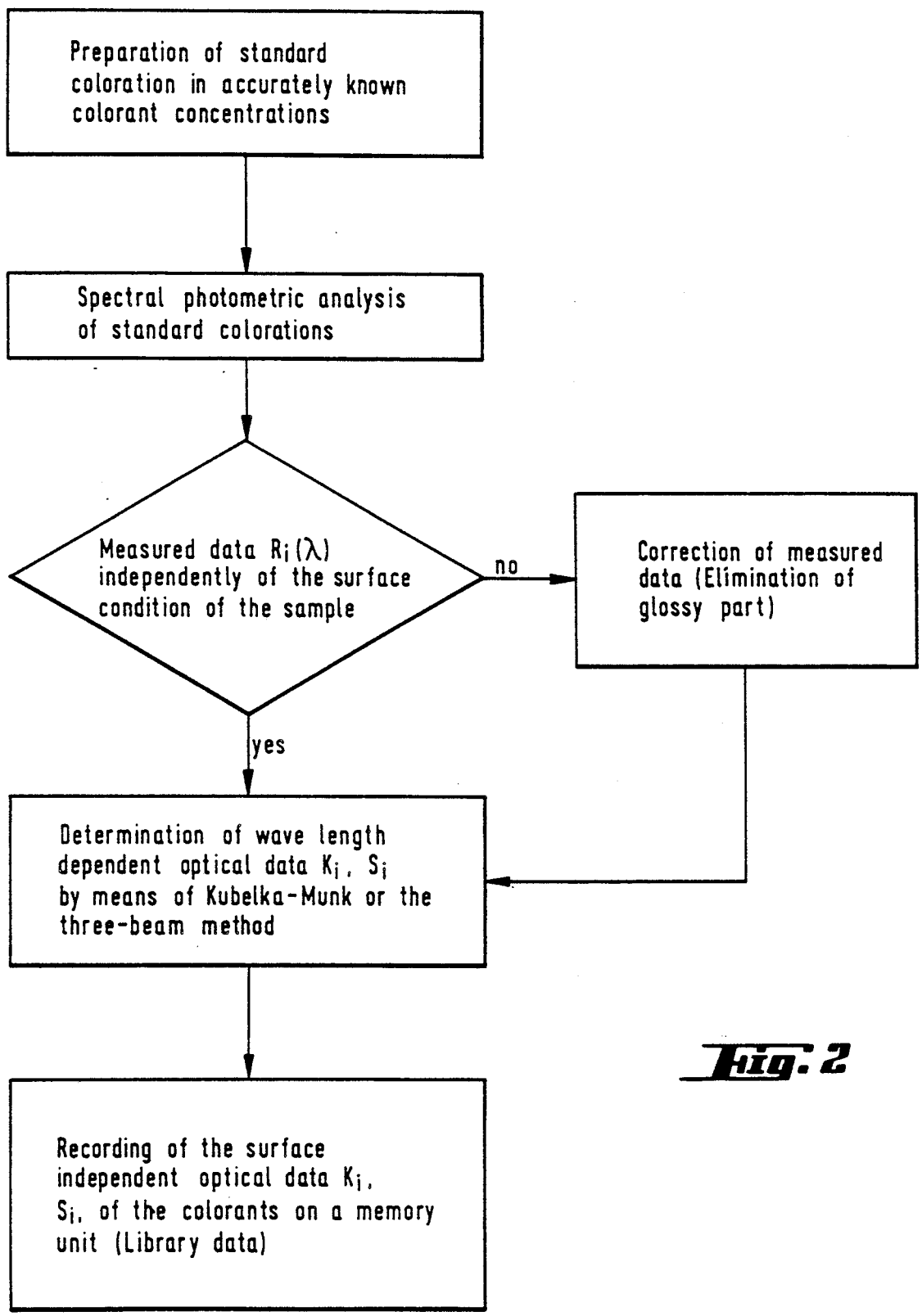
FIG. 2 shows a fundamental flow diagram of the determination of the optical data of the colorants; and, FIG. 3 shows a fundamental flow diagram of the preparation of the colorant concentrations.

In FIG. 2 a fundamental flow diagram for the determination of the optical data (absorption coefficient $K_i$ and scatter coefficient $S_i$) of the colorants i is shown. From the available colorants i, calibrated colorations are prepared in accurately known standard coloration concentrations and analyzed spectrophotometrically. This analysis may be carried out with a measuring layout according to FIG. 1, without the gloss component of the reflected light, but it can also be effected with a conventional integrating-sphere geometry, wherein the gloss is also measured and the measured results are therefore dependent on the surface condition of the sample (of the calibrated coloration). Consequently these conventionally determined data must be corrected prior to their further processing. These measured data, rendered surface state independent in this manner, may be further processed by different models. Usually, the Kubelka-Munk two-constant theory is used. The latter is also described in the aforecited publication of the Bundesanstalt fur Materialprüfung, Berlin or in an article by Dr. Ludwig Gall in Farbe und Lack, Vol. 80, No. 4, 1974, pages 297–306. A particularly appropriate compromise relative to accuracy between the two-constant theory and the multiple constant theory, which takes into consideration additional parameters, is represented by the three-beam theory according to Dr. D. Eitle and Dr. H. Pauli, known in particular from Colour 73, Adam Hilger, London 1973, pages 423 to 426 and a preprint of a paper presented at the FATIPEC XIV Congress, Budapest 1978, pages 209 to 213. In this manner, wavelength dependent optical data (absorption coefficient $K_i$ and scatter coefficient $S_i$) are obtained, but these are now independent of surface conditions. The optical data $K_i$, $S_i$ are stored for later use in a memory unit 15 as library data.

Figure 3:
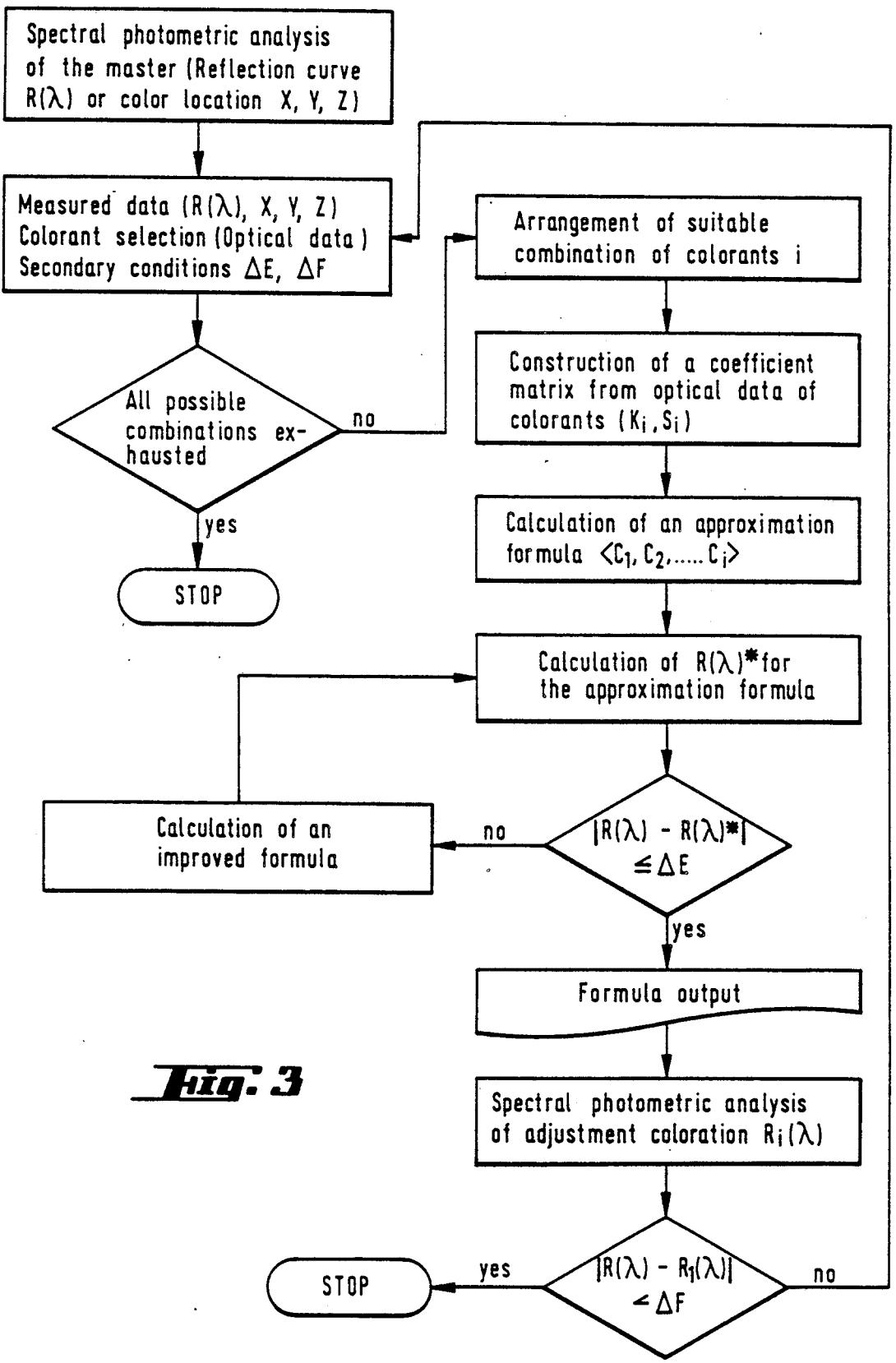

In FIG. 3 a fundamental flow diagram for the preparation of color formulations is shown. The spectrophotometric analysis of the master 6 is carried out in measuring layout according to FIG. 1 or preferably in a spectrophotometer SPM 100 of Gretag AG, Regensdorf, Zurich. The measured values (reflection curve R ($\lambda$) or colorimetric measures X, Y, Z) are fed into the computer unit, together with surface condition independent optical data $K_i$, $S_i$ of the available colorants i and other limiting conditions, such as the type of the combination to be formed (3 or 4 colorants or other combinations), combination rules (only colorants i of different colorant groups) or the cost of colorants i, and with an iteration threshold value $\Delta E$ and a minimal color deviation $\Delta F$ as additional conditions. Then the calculation is accomplished. If after this all possible combinations are exhausted, the master cannot be reproduced with the available colorants i. This, however, is not usually the case and thus the next step consists of the combination of suitable colorants and the construction of a coefficient matrix from the known $K_i$, $S_i$ of the combined colorants i. The calculation of the coefficients, preferably by the three-beam theory, yields a first approximation formula $C_1, C_2 \ldots C_i$. With this formula a fictitious reflections curve $R(\lambda)^*$ is calculated and compared with the $R(\lambda)$ measured on the master. If the difference between the two reflection curves $R(\lambda)$, $R(\lambda)^*$ is larger than the iteration threshold value $\Delta E$, an improved formula is calculated and the process repeated. If the difference between the two reflection curves $R(\lambda)$, $R(\lambda)^*$ is smaller than or equal to the iteration threshold value $\Delta E$, the color formula C is displayed on a display unit 14. The coloration is adjusted in keeping with this formula $C_1, C_2, \ldots C_i$. The subsequent second sample 61 is again analyzed spectrophotometrically and the second reflection curve $R_1(\lambda)$ compared with the reflection curve $R(\lambda)$ of the master 6. If the difference is less than the predetermined minimum color deviation $\Delta F$, the adjustment is considered to be successful; if not, the input data (for example the iteration threshold value $\Delta E$, secondary conditions or even the minimum color deviation $\Delta F$) must be reexamined, adjusted and the entire process repeated.

Altogether, the process according to the invention represents a significant simplification of the preparation of color formula, as already during the measurement the gloss component of the reflected light is suppressed and it is possible to work with a single set of optical data $K_i$, $S_i$ of the colorants independent of surface conditions. The use of the spectrophotometer SPM 100 of Gretag AG, Regensdorf/ Zürich as the analytical instrument provides further advantages in handling. The entire measuring layout including the computer, memory and display units, is readily transported and may be used universally and most importantly in a decentralized manner, on site.

It will be appreciated by those of ordinary skill in the art that the present invention can be embodied in other specific forms without departing from the spirit or essential characteristics thereof. The presently disclosed embodiments are therefore considered in all respects to be illustrative and not restrictive. The scope of the invention is indicated by the appended claims rather than the foregoing description, and all changes that come within the meaning and range of equivalents thereof are intended to be embraced therein.

What is claimed is:

1. A process for the preparation of color formula for the reproduction of the color of a master by the mixing of suitable concentrations of colorants, in particular colorings and pigments, said process comprising the steps of:

exposing a master or a sample by a source of directional measuring light, the measuring light being polarized in a first polarizer prior to impacting the master or sample, respectively;

passing light directionally reflected by the master or sample to a detector, said reflected light being passed through a second polarizer serving as an analyzer prior to its spectral decomposition by a wavelength dispersing element;

producing spectral measuring data from said reflected light;

converting said spectral measuring data in a computer unit into concentrations of colorants having known optical data previously calculated by spectro-photometric analysis via calibrated colorations using known standard colorant concentrations, and using optical data of the colorants independent of surface conditions;

comparing a sample adjusted in accordance with the converted colorant concentrations calculated spectrophotometrically with the master;

correcting the colorant concentrations in keeping with differences measured;

repeating the correction process until the difference measured is less than a predetermined minimum color deviation.

2. The process according to claim 1, further comprising the step of determining the optical data of the colorants from measured data obtained from a spectrophotometric analysis of the colorants with polarized measuring light and polarized reflected light.

3. The process according to claim 2, wherein the measuring light is incident at an angle of $0° \pm 10°$ relative to a normal onto the sample, and the reflected light is detected at an angle of 45°±5° relative to the normal of the sample and passed to the detector.

4. Process according to claim 2, wherein the measuring light is incident at an angle of 45°±10° relative to a normal onto the sample, and the light reflected is detected at an angle of 0°±10° relative to the normal of the sample and passed to the detector.

5. The process according to claim 1, wherein the measuring light is incident at an angle of 0°±10° relative to a normal onto the sample, and the reflected light is detected at an angle of 45°±5° relative to the normal of the sample and passed to the detector.

6. Process according to claim 1, wherein the measuring light is incident at an angle of 45°±10° relative to a normal onto the sample, and the light reflected is detected at an angle of 0°±10° relative to the normal of the sample and passed to the detector.

7. An apparatus for the preparation of color formula for the reproduction of the color of a master by the mixing of suitable concentrations of colorants, in particular colorings and pigments, said apparatus comprising:
- a computer unit;
- a display;
- a memory unit;
- a spectrophotometer, said spectrophotometer being equipped with a first and a second polarizer, said first polarizer being located in a measuring beam path in front of a sample and the second polarizer being located in a beam path of reflected light in front of a wavelenth dispersing element; and,
- means for coupling said spectrophotometer with said computer unit, said display and said memory unit.

8. The apparatus according to claim 7, wherein said means for coupling is a serial interface.

9. The apparatus according to claim 7, wherein said sample is a master.

10. The apparatus according to claim 7, wherein said sample is an adjusted sample.

* * * * *